US012631656B2

(12) United States Patent     (10) Patent No.:   US 12,631,656 B2

Datki et al.     (45) Date of Patent:    May 19, 2026

---

(54) METHOD FOR DIAGNOSING ALZHEIMER'S DISEASE SPECTRUM NEUROCOGNITIVE DISORDERS FROM TEAR SAMPLE, AND SOLUTION AND DIAGNOSTIC KIT USEFUL IN THE METHOD

(71) Applicant: Szegedi Tudományegyetem, Szeged (HU)

(72) Inventors: Zsolt Datki, Szeged (HU); János Kálmán, Szeged (HU); Magdolna Pákáski, Szeged (HU)

(73) Assignee: Szegedi Tudomanyegyetem, Szeged (HU)

( * ) Notice: Subject to any disclaimer, the term of this patent is extended or adjusted under 35 U.S.C. 154(b) by 953 days.

(21) Appl. No.: 17/787,991

(22) PCT Filed: Dec. 22, 2020

(86) PCT No.: PCT/HU2020/000039

§ 371 (c)(1),
(2) Date: Jun. 22, 2022

(87) PCT Pub. No.: WO2021/130508

PCT Pub. Date: Jul. 1, 2021

(65) Prior Publication Data

US 2023/0024661 A1    Jan. 26, 2023

(30) Foreign Application Priority Data

Dec. 23, 2019   (HU) .................................... P1900450

(51) Int. Cl.
*G01N 21/64*     (2006.01)
*B82Y 5/00*     (2011.01)
(Continued)

(52) U.S. Cl.
CPC ............................... *G01N 33/6896* (2013.01)

(58) Field of Classification Search
CPC .. G01N 33/6896; G01N 33/48; A61B 5/4088; C01G 5/00; C01G 7/00; C01G 9/00
See application file for complete search history.

(56) References Cited

U.S. PATENT DOCUMENTS

2010/0311688 A1* 12/2010 Chapin .................. A61K 47/38
514/57

OTHER PUBLICATIONS

European Patent Office, International Search Report in PCT Application No. PCT/HU2020/000039, Jun. 29, 2021 (3 pgs.).

(Continued)

*Primary Examiner* — Jennifer Wecker
*Assistant Examiner* — Oyeleye Alexander Alabi
(74) *Attorney, Agent, or Firm* — Wood Herron & Evans LLP

(57) ABSTRACT

The invention relates to an aqueous solution of $AuCl_3 \times 2H_2O$ or $HAuCl_4 \times 4H_2O$, $ZnCl_2$ or $ZnSO_4$, and $AgNO_3$ having an $Au^{3+}$ concentration of 0.8 mM-1.6 mM, a $Zn^{2+}$ concentration of 15 μM-50 μM, and an $Ag^+$ concentration of 5 μM-50 μM. The invention extends to a kit comprising a solution of the invention, a method of preparing said solution, and the use of a solution of the invention, a solution prepared by a method of the invention, or a kit of the invention in predicting and/or diagnosing and/or monitoring a neurocognitive disorder of the Alzheimer's disease spectrum. The invention extends to a method for predicting and/or diagnosing and/or monitoring a neurocognitive disorder of the Alzheimer's disease spectrum in a patient comprising contacting a tear sample from the patient normalised for protein concentration with a solution of the invention; applying an amount of the tear sample thus obtained to a surface; allowing the tear sample to dry; and drawing a conclusion based on the pattern of the thus obtained dried tear sample, whether the patient is at risk of or suffers from a neurocognitive disorder of the Alzheimer's disease spectrum.

7 Claims, 5 Drawing Sheets

(51) Int. Cl.

| | |
|---|---|
| *B82Y 30/00* | (2011.01) |
| *B82Y 40/00* | (2011.01) |
| *C07F 5/02* | (2006.01) |
| *C09B 57/00* | (2006.01) |
| *C09K 11/06* | (2006.01) |
| *G01N 1/30* | (2006.01) |
| *G01N 15/10* | (2024.01) |
| *G01N 15/1429* | (2024.01) |
| *G01N 27/626* | (2021.01) |
| *G01N 31/22* | (2006.01) |
| *G01N 33/483* | (2006.01) |
| *G01N 33/543* | (2006.01) |
| *G01N 33/58* | (2006.01) |
| *G01N 33/68* | (2006.01) |

(56) References Cited

OTHER PUBLICATIONS

International Preliminary Report on Patentabiliy in PCT Application No. PCT/HU2020/000039 (7 pgs.).

Kenny Aidan et al: "Proteins and microRNAs are differentially expressed in tear fluid from patients with Alzheimer's disease," Scientific Reports, vol. 9, No. 1, Oct. 28, 2019, XP55810387, DOI: 10.1038/s41598-019-51837-y: URL:http://www.nature.com/articles/s41598-019-51837-y (14 pgs.).

Gergo Kallo et al: "Changes in the Chemical Barrier Composition of Tears in Alzheimer's Disease Reveal Potential Tear diagnostic Biomarkers," Plos One, vol. 11, No. 6, Jun. 21, 2016, pp. 1-14, XP055709430, DOI: 20/1371/journal.pone.0158000 (7 pgs.).

Gijs Marlies et al: "Differences in tear protein biomarkers between patients with Alzheimer's disease and controls," XP002803180, Biosciences Information Service, Philadelphia, PA, US: Jul. 2019 (2 pgs.).

Hungarian Intellectual Property Office, Search Report in HU Application No. P1900450, Feb. 11, 2020 (2 pgs.); Preliminary Opinion, Feb. 24, 2020 (4 pgs.); Examination Report, Apr. 10, 2022 (4 pgs.).

Mihaly G.: Ujszeru metodikai lehetosegek konnymintabol Alzheimer-kor szuresere; Yokouchi, N.: Tear stagogram assay recognizes vascular dementia, TDK Konferencia (SZTE AOK) (Nov. 13, 2019) (2 pgs.).

Haeringen: Clinical biochemistry of tears, Surv. phthal., 26(2), 84-86 (1981) (7 pgs.).

Kodama: Studies on the Interaction between Heavy Metal Salt and Protein, J. Biochem., 2(3), 505-524 (1923) az egesz dokumentum, kulonosen az 1. abra (10 pgs.).

Lengfeld: On Gold Halides, Am. Chem. J., XXVI, 324-332 (1901) (5 pgs.).

* cited by examiner

Summary

File   Edit   Font

| | Slice | Count | Total Area | Average Size | %Area |
|---|---|---|---|---|---|
| Non-AD | QTD_SC_012 (8).TIF | 1350 | 154701.515 | 114.594 | 75.840 |
| AD | QTD_AD_019 (6).TIF | 35115 | 66802.880 | 1.902 | 32.749 |

Control = 109.264 (SEM = +/- 1.8879)

| Non-AD | V = (114.594 / 109.264) × 100 = 104.878 % |
|---|---|
| AD | V = (1.902 / 109.264) × 100 = 1.741 % |

METHOD FOR DIAGNOSING ALZHEIMER'S DISEASE SPECTRUM NEUROCOGNITIVE DISORDERS FROM TEAR SAMPLE, AND SOLUTION AND DIAGNOSTIC KIT USEFUL IN THE METHOD

This application claims priority, under Section 371, and/or as a continuation under Section 120, to PCT Application No. PCT/HU2020/000039, filed on Dec. 22, 2020, which claims priority to Hungarian Application No. P1900450 HU, filed on Dec. 23, 2019.

TECHNICAL FIELD

The invention relates to a multi-component solution and a kit useful in the diagnosis and/or prediction and/or monitoring of neurocognitive disorders of the Alzheimer's disease spectrum (AD spectrum neurocognitive disorders) including also the genetic forms of Alzheimer's disease, Down's syndrome depending on age, isolated and combined cerebral amyloidopathies, tauopathies, the combined manifestation of Alzheimer's disease with type II diabetes mellitus, and the manifestation of mild cognitive disorder (MCD) related to Alzheimer's disease; as well as to a method of preparing the solution, to a method of diagnosing and/or predicting and/or monitoring a neurocognitive disorder of the Alzheimer's disease spectrum, and to the use of the solution or kit in a method of diagnosing and/or predicting and/or monitoring a neurocognitive disorder of the Alzheimer's disease spectrum. The invention also relates to the preparation of a dried tear sample using the solution or kit.

BACKGROUND OF THE INVENTION

Today, an estimated 50 million people worldwide suffer from dementia (major neurocognitive disorder), which will increase to approximately 75 million by 2030. In 2015, the costs of MCD care amounted to USD 818 billion, which is 1% of the global GDP. Among the underlying aetiological factors of neurocognitive disorders, Alzheimer's disease (AD, Alzheimer's, Alzheimer's dementia) is the most common being responsible for 70% of the cases. Alzheimer's disease is a form of dementia. Several other forms of dementia are also known: the medical science distinguishes more than 50 of them. Alzheimer's disease is the most prevalent type of dementia in the Western Hemisphere, and also in Hungary. The second most prevalent form is dementia of vascular origin, i.e. vascular dementia. The two most frequent forms, that is, Alzheimer's disease and vascular dementia very often show a mixed manifestation simultaneously occurring in the very same patients. The risk of developing AD is very high in type 2 diabetes mellitus (T2DM), for example, which currently affects 382 million people worldwide and is expected to increase to 592 million by 2035 (Roy S, Kim N, Desai A, Komaragiri M, Baxi N, Jassil N, Blessinger M, Khan M, Cole R, Desai N, Terrigno R, Hunter K. Cognitive Function and Control of Type 2 Diabetes Mellitus in Young Adults, 2015). The AD-associated cognitive decline primarily affects the population of over-65s; however, the prodrome stage, the mild cognitive disorder (MCD) occurs also in 20% of the individuals below the age of 60 suffering from T2DM (Roy, 2015, see above). The early and very mild form of Alzheimer's disease associated with few clinical symptoms is referred to as mild cognitive disorder (MCD) by clinicians.

As regards Alzheimer's dementia, Down's syndrome represents a special situation. Up to an age of 30 to 40, individuals with Down's syndrome do not behave like those with Alzheimer's disease as regards their symptoms and clinical picture; then, after the age of 40, they very shortly begin to show the clinical, neurobiological and neuropathological symptoms of Alzheimer's disease, in most cases as part of a rapid ageing process. Therefore, Down's syndrome is also considered as a genetic form of Alzheimer's disease with an age-dependent manifestation. Thus, Down's syndrome is classified as a neurocognitive disorder of the Alzheimer's disease spectrum depending on age.

Diagnosing Alzheimer's disease in living individuals is a medical work (and cannot be replaced by any known diagnostic methods), diagnosis is formulated by a clinician on the basis of combining an examination of the physical and mental functions of the patient with the results of instrument-based patient examination methods. Such diagnosis made by a clinical physician is referred to as a "clinical diagnosis of Alzheimer's disease". The clinical diagnosis of Alzheimer's disease is therefore a medical analysis task. Its diagnostic accuracy is not 100%, therefore the literature refers to the clinical diagnosis of Alzheimer's disease as a "probability diagnosis", and distinguishes between "probability" diagnosis and "possible" diagnosis of Alzheimer's disease. According to the current diagnostic protocols, the clinical diagnosis of Alzheimer's disease (AD) is based on medical analysis being a synthesis of the results of the clinical anamnesis, laboratory tests, neurological, psychiatric and physical examinations, cognitive tests, and brain imaging (CT, MR) examinations. According to current knowledge, the clinical diagnosis of Alzheimer's disease cannot be replaced by any diagnostic methods per se; currently known Alzheimer diagnostic methods contribute to the diagnostic accuracy in the form of the sensitivity and specificity of the given method. The diagnosis of MCD is also clinical in nature, and being based on a few symptoms, it is even less certain than the clinical diagnosis of AD. This situation is further complicated by the fact that clinicians distinguish different forms of MCDs, and not all MCD patients will become AD patients or patients with other forms of dementia. In the routine diagnosis of MCD and AD, psychometric test are used to assess the extent of the neurocognitive disorder, and brain imaging (CT, MRI) examinations are used to identify the underlying specific disease. In clinical studies with a scientific purpose, such diagnostic methods are extended to include liquor diagnostics requiring a painful lumbar puncture, or a considerably expensive PET examination. In Hungary, psychological tests, cerebral neuroradiological imaging examinations (CT, MRI, SPECT, PET), and brain liquor sampling methods, having different sensitivity and specificity indicators, are currently used for the clinical diagnosis of Alzheimer's disease. The only certain diagnosis of Alzheimer's disease is based on the histological examination of the brain after the patient's death (unfortunately, it was in recent years that it was demonstrated that not even the histological diagnosis is so 100% clear-cut as it had been believed before). The attention of the clinicians of the world is focused on the early discovery of Alzheimer's disease even in the symptom-free phase, that is, MCD or pre-MCD discovery is the optimal goal in order to achieve higher therapeutic success rates and to facilitate prevention.

Some of the research on Alzheimer's disease was directed to the testing of tear samples. The majority of this research consists of mass spectrometry (MS) or chromatographic (HPLC) measurements. Scientists tried to isolate the components (lipids, electrolytes, and proteins) in the samples with the expectation of finding some AD-specific biomarker molecules. Based on literature data and our own MS measurements, we can conclude that no practical breakthrough of diagnostic relevance has ever been achieved by anyone in this field.

The testing of the patterns of native dried tear samples has already been described by many (Nom M., Ferning in conjunctival-cytologic preparations. Crystallization in stained semiquantitative pipette samples of conjunctival fluid. Acta Ophthalmologica 1987; 65:118-23), but not in relation to Alzheimer's disease or to neurocognitive disorders of the Alzheimer's disease spectrum. From the time of the first documented testing of native dried tear samples [Fourcroy A F, Vauquelin L N. Examen chimique des larmes et de l'humeur des narines (Chemical examination of tears and nasal humor). Ann Chim (Paris) 1791; 10:113-30)], several attempts were made to analyse the patterns and to use them as diagnostic markers [Solé A. Die Stagoskopie der Tränen (The stagoscopy of tears). Klin Monatsbl Augenheilkd 1955; 126:446-51; Tabbara K F, Okumoto M. Ocular ferning test. A qualitative test for mucous deficiency. Ophthalmology 1982; 89:712-7; Rolando M, Baldi F, Calabria G. Tear mucus crystallization in children with cystic fibrosis. Ophthalmologica 1988; 197:202-6; Golding T R, Brennan N A. The basis of tear ferning. Clin Exp Optom 1989; 72:102-12; Puderbach S, Stolze H H. Tear ferning and other lacrimal tests in normal persons of different ages. Int Ophthalmol 1991; 15:391-5]. The real difficulty is posed by the intra- and interpersonal variability of the patterns of dried tears (stagograms) as shown in FIG. 1.

In an approach, the patterns of native dried teardrops were divided into 3 to 4 zones (qualitative analysis), and then the arborisation of the "fern pattern" into 4 types (semiquantitative analysis). Said analyses can be used as supporting and prescreening tests in ophthalmological diseases, but are completely unsuitable for the diagnosis of a neurocognitive disorder of the Alzheimer's disease spectrum, for example. They are not sensitive enough and not at all quantitative due to the relatively "coarse" division and the large-scale classification.

BRIEF DESCRIPTION OF THE INVENTION

The purpose of the invention is to facilitate the medical diagnostic work related to neurocognitive disorders of the Alzheimer's disease spectrum, as outlined above, especially Alzheimer's disease (McKhann G, Drachman D, Folstein M, et al. Clinical diagnosis of Alzheimer's disease: report of the NINCDS-ADRDA Work Group under the auspices of Department of Health and Human Services Task Force on Alzheimer's Disease. Neurology 1984; 34:939-44), and to completely or partially replace expensive and/or painful examinations.

We have realised that the divergence-based former logical concept related to the testing of tear samples should be inverted, that is, an additive, convergent, i.e. conglomerated projection of the properties of the tear sample should be studied, which is based on the preparation, drying and analysis of the sample. We have found that these processes involve a number of molecular and ionic interactions, which result in a specific pattern based on the qualitative and quantitative properties of the components.

The stagogram concept was considered good, and therefore it was decided to eliminate the limitations arising from diversity. We have found that homogenisation of the tear samples and, thus, that of the forming pattern is of key importance in ensuring the interpersonal comparability of the resulting patterns yet bearing sufficient specific information to enable a differential diagnosis.

The pattern of the native dried tear is primarily determined by lipids and electrolytes (salt content). If the sample is diluted in order to dampen the effects and influence of these components, the protein content (concentration) will also decrease. Even if in a diluted form, samples are so diverse and produce such varied patterns, and have so high individual variability, that a comparison with sufficient objectivity is impossible.

Although it is well known that patients characterisable with a neurocognitive disorder of the AD spectrum show a higher mean protein concentration in the tear samples than patients not characterisable with such a disorder ("control"), the SD thereof is so large that the diagnostic use of the protein content is prevented from a statistical point of view.

Our tests carried out using native tear samples (not treated with L-AD solution) showed that controls (where normalisation required high dilutions) with a protein content (e.g. 11 mg/mL) exceeding the mean of the patients suffering a neurocognitive disorder of the AD spectrum also produce dark (dense) stagograms, while a population of patients with a low protein content (e.g. 1.5 mg/mL) and suffering from a neurocognitive disorder of the AD spectrum (where dilution was not necessary at all) also produced sparse (light) stagograms.

Based on these results, we have found that the intrinsic substances (e.g. chloride ions) themselves of the original tear samples are unable to produce stagograms that would enable a differentiation between patients characterisable with a neurocognitive disorder of the AD spectrum and patients (individuals) not characterisable with such a disorder ("healthy patients").

We have realised that the effects of lipids and electrolytes ($Na^+$, $Ca^{2+}$, $Mg^{2+}$, $Cl^-$) on the stagogram need to be reduced, and, at the same time, the additive effect of the total protein content (i.e. the proteins of the tear) should be dominant on the pattern formation.

We have found that a dried tear sample must comply with the following criteria to enable to detect a meaningful difference between healthy individuals and patients characterisable with a neurocognitive disorder of the AD spectrum, especially patients with Alzheimer's disease:
 a. a structured structure that forms a homogeneous pattern within the drop is necessary;
 b. it must show a difference in comparison with the native dried tear sample;
 c. it must show a difference for patients characterisable with a neurocognitive disorder of the AD spectrum in comparison with the control;
 d. the structured pattern should be primarily determined by the protein content;
 e. the samples need to be normalised for protein concentration in order to eliminate the differences arising from quantities.

We have found that it is the preparation of the sample that leads to interpersonal comparability of the forming patterns while the patterns also bear sufficient specific information for a differential diagnosis.

The prior art does not provide any teaching as to which salts tear proteins form a precipitate with. In general, these proteins are highly varied in terms of the salts that they form a precipitate with. We have found that $AuCl_3$ and $HAuCl_4$ salts precipitate tear proteins; however, a treatment of the tear samples with a solution of these salts (including hydrate forms, e.g. $AuCl_3 \times 2H_2O$ or $HAuCl_4 \times 4H_2O$) per se does not produce a homogeneous stagogram. However, it was observed that the stagograms of patients characterisable with a neurocognitive disorder of the AD spectrum show some density differences in comparison with the stagograms of patients not characterisable with such a disorder. Thus, additionally, we have found that in order to prepare stagograms suitable for diagnostic purposes, tear samples must be treated with a combination solution (reagent) further comprising other metal salt beyond the above-mentioned gold salt.

We have found that an aqueous solution comprising $Au^{3+}$, $Zn^{2+}$ and $Ag^{+}$ must be added to the tear sample in the form of an aqueous solution of $AuCl_3 \times 2H_2O$ or $HAuCl_4 \times 4H_2O$, zinc chloride or zinc sulphate, and silver nitrate containing $Au^{3+}$, $Zn^{2+}$ and $Ag^{+}$ at specific concentrations. Upon interaction with the tear sample normalised for protein amount (protein concentration), these are able to detect differences of diagnostic power between healthy individuals and patients characterisable with a neurocognitive disorder of the AD spectrum, especially Alzheimer's disease, at a sufficiently high specificity and sensitivity. Namely, tear samples normalised for protein amount and treated with said aqueous solution produce stagograms that are useful in the prediction and/or diagnosis and/or monitoring of a neurocognitive disorder of the Alzheimer's disease spectrum.

We have found that zinc ion is not only relevant as protein precipitating element but also maintains the balance of the standard potential of the solution as long as we stick to the order of gold-silver-zinc when preparing the solution, that is, the components of the solution are added in that order. We have also determined in which order and concentrations the components must be combined during the preparation to produce a homogeneous solution, and thus to obtain a homogeneous pattern (stagogram)—that is, one which is suitable for the above diagnostic, predictive and monitoring purposes—with the use of the solution.

The above findings resulted in the present invention, more specifically in the products, methods, and uses according to the main claims, by which the purposes of the invention are achieved. Certain preferred embodiments of the invention are defined in the dependent claims.

In a first aspect, the invention relates to an aqueous solution of (a) $AuCl_3 \times 2H_2O$ or $HAuCl_4 \times 4H_2O$, preferably $AuCl_3 \times 2H_2O$, (b) $ZnCl_2$ or $ZnSO_4$, preferably $ZnCl_2$, and (c) $AgNO_3$, which comprises $Au^{3+}$ at a concentration of about 0.8 mM to 1.6 mM, $Zn^{2+}$ at a concentration of about 15 μM to 50 μM, and $Ag^{+}$ at a concentration of about 5 μM to 50 μM; preferably, the solution comprising $Au^{3+}$ at a concentration of about 1 mM, $Zn^{2+}$ at a concentration of about 20 μM, and $Ag^{+}$ at a concentration of about 40 μM.

The invention also relates to a method of preparing an aqueous solution of $AuCl_3 \times 2H_2O$ or $HAuCl_4 \times 4H_2O$, $ZnCl_2$ or $ZnSO_4$, and $AgNO_3$, the solution comprising $Au^{3+}$ at a concentration of about 0.8 mM to 1.6 mM, $Zn^{2+}$ at a concentration of about 15 μM to 50 μM, and $Ag^{+}$ at a concentration of about 5 μM to 50 μM, preferably, $Au^{3+}$ at a concentration of about 1 mM, $Zn^{2+}$ at a concentration of about 20 μM, and $Ag^{+}$ at a concentration of about 40 μM, wherein the method comprises (a) dissolving $AuCl_3 \times 2H_2O$ or $HAuCl_4 \times 4H_2O$ in distilled or deionised water to obtain a solution with an $Au^{3+}$ concentration of about 2 to 4 mM;

(b) optionally freezing the solution at a temperature of about −20° C., and then thawing it before step (c);

(c) filtering the solution with the $Au^{3+}$ concentration of about 2 to 4 mM through a bacterial filter (with a maximum pore size of 0.45 μm), and then mixing it with distilled or deionised water to obtain a solution with an $Au^{3+}$ concentration of about 0.8 to 1.6 mM;

(d) adding a solution with a $Zn^{2+}$ concentration of about 50 mM prepared using $ZnCl_2$ or $ZnSO_4$ and distilled or deionised water to the solution with the $Au^{3+}$ concentration of about 0.8 to 1.6 mM in order to prepare a solution with a $Zn^{2+}$ concentration of about 15 to 50 μM;

(e) adding a solution with an $Ag^{+}$ concentration of about 50 mM prepared using $AgNO_3$ and distilled or deionised water to the solution with the $Au^{3+}$ concentration of about 0.8 to 1.6 mM and $Zn^{2+}$ concentration of about 15 to 50 μM, and the solution thus obtained is optionally stirred.

The invention also relates to a kit comprising the solution according to the invention. The kit is useful in the diagnostic, predictive, or monitoring method of the invention. The kit may also comprise one or more of the following: a container (e.g. 0.2-mL Eppendorf tube), a dropper, a carrier with a hydrophobic surface, preferably a carrier with a hydrophobic plastic surface, e.g. hydrophobic plastic carrier (e.g. made of polystyrene, e.g. Petri dish made of polystyrene) for drying the tear sample, a capillary tube (e.g. glass capillary), a disinfectant (e.g. ethanol-based disinfectant), instructions for use.

In another aspect, the invention relates to a method for the preparation of a dried tear sample using the solution or the kit of the invention. Said method of the invention for preparing dried tear sample comprises normalising a native tear sample for protein concentration (1.5 mg/mL to 15 mg/mL, preferably 1.5 mg/mL), then contacting (treating, preferably mixing) it with a solution of the invention as defined above (also called an L-AD solution), wherein the L-AD solution is preferably an aqueous solution of $AuCl_3 \times 2H_2O$, $ZnCl_2$ and $AgNO_3$, and preferably, in the solution the concentration of $Au^{3+}$ is 1 mM, the concentration of $Zn^{2+}$ is 20 μM, and the concentration of $Ag^{+}$ is 40 μM, then applying an amount, preferably an amount of an about 1-μL, of the contacted and normalised tear sample to a surface, preferably a hydrophobic plastic surface, and then allowing to dry. Preferably, the ratio between the volume of the sample and the volume of the L-AD solution in the contacting step is about (0.9 to 1.1):(6 to 7), preferably 1:6.5.

The term "normalising for protein concentration" refers to adjusting the total protein concentration of the native tear sample to a chosen value. When comparing two or more dried tear samples or the values calculated from them (e.g. average particle size), or when averaging such values, the total protein concentrations need to be identical.

In a further aspect, the invention relates to the use of the solution or kit of the invention, or a dried tear sample prepared by the method of the invention in a method for predicting or diagnosing or monitoring a neurocognitive disorder of the Alzheimer's disease spectrum in a patient.

In a yet further aspect, the invention relates to a method for predicting and/or diagnosing and/or monitoring a neurocognitive disorder of the Alzheimer's disease spectrum in a patient (in an individual). The method comprises (a) normalising a tear sample from the patient for protein concentration (1.5 mg/mL to 15 mg/mL, preferably 1.5 mg/mL);

(b) the normalised tear sample is contacted, preferably mixed with a solution of the invention;

(c) applying an amount of the contacted normalised tear sample, preferably an amount of about 1 μL, to a surface, preferably a hydrophobic plastic surface;

(d) allowing the applied tear sample to dry;

(e) drawing a conclusion on the basis of the pattern of the thus obtained dried tear sample or of the pattern of an image of the thus obtained dried tear sample whether the patient is at risk of or suffers from a neurocognitive disorder of the Alzheimer's disease spectrum (whether there is a presence of a risk of a neurocognitive disorder of the Alzheimer's disease spectrum for the patient or whether there is a presence of a neurocognitive disorder of the Alzheimer's disease spectrum in the patient). A method of the invention for predicting and/or diagnosing and/or monitoring a neurocognitive disorder of the Alzheimer's disease spectrum is an in vitro method.

DETAILED DESCRIPTION OF THE INVENTION

Figure 1:
FIG. 1 shows images of patterns of dried native tear samples (own photographs, magnification: 64×, 16 bit RAW). The variability problem can be clearly observed.

The aqueous solution defined in the appended claims is a solution of the components defined in said claims prepared using distilled or deionised water. The aqueous solution is prepared with the exclusive use of the listed salts (that is, $AuCl_3 \times 2H_2O$ or $HAuCl_4 \times 4H_2O$, preferably $AuCl_3 \times 2H_2O$; $ZnCl_2$ or $ZnSO_4$, preferably $ZnCl_2$; and $AgNO_3$).

Thus, the method, solution and kit of the invention are useful in the prediction and/or diagnosis and/or monitoring of a neurocognitive disorder of the Alzheimer's disease spectrum [e.g. Alzheimer's disease or mild cognitive disorder (MCD)], on the basis of a sample of human tear. The prediction, diagnosis or monitoring of the neurocognitive disorder of the AD spectrum refers—in relation to a neurocognitive disorder of the Alzheimer's disease spectrum—to predicting, diagnosing, or monitoring by the use of the L-AD method as an independent method, as well as to predicting, diagnosing, or monitoring by the use of the L-AD method as a method supporting other diagnostic methods.

In the description and the claims, the term "tear sample" also covers a supernatant obtained by centrifuging tear taken from a patient. Therefore, as the tear sample of the invention, one may use the original tear sample, optionally upon freezing and thawing, or the supernatant obtained by centrifuging the original, optionally frozen and thawed tear sample. In the latter case, the supernatant or a part thereof is normalised for protein concentration, and is treated with a solution of the invention. In another embodiment, the original tear sample from the patient is dried, for example, for the purposes of transport and/or storage, and is later reconstituted before use (testing). Thus, the tear sample used according to the invention may be fresh tear, stored tear, frozen and thawed tear, dried and reconstituted tear, or a supernatant obtained by centrifuging any of these. All of the above can be referred to as a native tear sample as long as they are not treated with L-AD solution or other salt solution.

The solution of the invention (also referred to as "L-AD solution") is preferably prepared by dissolving $AuCl_3 \times 2H_2O$ with a minimum $Au^{3+}$ content of 57% and with a 40% compensation based on MW, in distilled water to obtain a solution with an $Au^{3+}$ concentration of 2 mM. Optionally, the solution thus obtained is frozen at a temperature of −20° C., and then thawed before further steps. The solution thus obtained is filtered through a filter with a pore size of 0.45 μm, and to 500 μL of this filtered solution 499.1 μL of distilled water is added, followed by the addition of 0.4 μL of a $ZnCl_2$ stock solution with a $Zn^{2+}$ concentration of 50 mM prepared in distilled water, then 0.8 μL of an $AgNO_3$ stock solution with an $Ag^+$ concentration of 50 mM prepared in distilled water, and finally the solution thus obtained is stirred by vortexing.

The L-AD solution has an antiseptic effect preventing it from becoming infected; it is also not light-sensitive, and can be stored at room temperature.

When using a solution of the invention, by the use of an L-AD solution or a kit, wherein the L-AD solution is preferably an aqueous solution of $AuCl_3 \times 2H_2O$, $ZnCl_2$ and $AgNO_3$, and preferably the concentration of $Au^{3+}$ is 1 mM, the concentration of $Zn^{2+}$ is 20 μM, and the concentration of $Ag^+$ is 40 μM, and the kit preferably comprises such an L-AD solution, a dried tear sample of the invention is prepared using a method comprising normalising a tear sample from a patient for protein concentration (1.5 mg/mL to 15 mg/mL, preferably 1.5 mg/mL), and then contacting the normalised tear sample with L-AD solution, the ratio between the volume of the sample and the volume of L-AD solution in the contacting step is preferably (0.9-1.1):(6-7), preferably 1:6.5, and then applying an amount, preferably an amount of about 1 μL, of the contacted and normalised tear sample to a surface; preferably a hydrophobic plastic surface, and the tear sample amount is allowed to dry.

The use of a hydrophobic plastic surface (e.g. polystyrene) during the preparation of the dried tear sample, that is, the application of the tear sample to a hydrophobic plastic surface showed the unexpected benefit of ringless stagograms. At the same time, native (i.e. not treated with L-AD solution), dried tear samples do not produce ringless stagograms even on hydrophobic plastic surfaces.

The method of preparing a dried tear sample of the invention preferably comprises the steps of
- a) centrifuging, preferably at 300×G for 3 minutes, a native tear sample from a patient, optionally after freezing and thawing, wherein freezing is carried out preferably at −20° C.;
- b) homogenising the supernatant of the sample thus obtained;
- c) optionally freezing the homogenised supernatant to a temperature at −75° C., and then thawing it;
- d) performing protein assay, preferably BisANS protein assay with an amount of the supernatant, preferably an amount of about 0.5 μL;
- e) normalising an amount, preferably an amount of about 1.4 μL of the homogenised supernatant to a pre-determined concentration, preferably 1.5 mg/mL, preferably using distilled water for the normalisation;
- f) adding an amount, preferably an amount of about 6.5 μL, of L-AD solution to an amount, preferably to an amount of about 1 μL, of the normalised supernatant, preferably while stirring with a pipette;
- g) applying, preferably pipetting, an amount, preferably an amount of about 1-μL, of the tear sample treated with the L-AD solution to a surface, preferably a hydrophobic plastic surface, more preferably a Petri dish made from such plastic;
- h) allowing the supernatant applied to the surface to dry, preferably for 20 minutes, preferably at a relative humidity of about 50% to obtain a dried tear sample of the invention;
- i) optionally archiving the dried tear sample of the invention thus obtained, optionally comprising sealing the Petri dish, preferably with parafilm, in case the dried tear sample of the invention is in the preferably used Petri dish.

Thus, typically, the dried tear sample is obtained by drying 1 μL of original normalised tear sample treated with L-AD solution or of normalised supernatant treated with L-AD solution, wherein the supernatant is obtained by centrifuging the original tear sample. The conditions under which the tear samples are dried are preferably as follows: relative humidity: 40% to 55%; temperature: room temperature, e.g. 24° C., with passive evaporation; drying time: at least 20 minutes, preferably at least 30 minutes.

When using a solution of the invention, i.e. the solution of various "reactive" ions (preferably in the ratio of $Au^{3+}:Zn^{2+}:Ag^+=50:1:2$), due to the properties of the components, a complex between the ion components of the multi-component solution and the tear proteins is formed, thereby creating a special structure depending on the number (amount) and position of the affected amino acids (cysteine, methionine, histidine, arginine). When preparing an L-AD solution—on the basis of the different standard potentials of the metal ions—, a fragile chemical balance is created. Since both the quantities and qualities of the given protein species are different (despite normalising the total protein amount), the pattern induced by the L-AD solution will also be individual and specific. The components of the L-AD solution bind to amino acids and form cross-bridges, and because different proteins have different and limited numbers of target amino acids, the patterns will also be different in the two groups. The number of epitopes affects the 3D structure as a differentiating factor. In a sample with a given protein content, the number of bonds created by the above-mentioned metal ions will be unique (first-degree specificity). Reactive ions unable to avoid molecular binding force proteins into unique spatial conformations depending on other native properties of the proteins (second-degree specificity). The quantitative and qualitative parameters of a given protein are not significantly different in the control and AD groups (groups of patients characterisable with a neurocognitive disorder of the Alzheimer's disease spectrum) (mass spectrometry results), but an additive measurement thereof already shows different patterns (third-degree specificity). In the world of molecules, crystallisation is among the most sensitive processes. Minimal disturbances (e.g. an extra component or the lack thereof) may also generate absolute differences in each property (shape, size, angles and number of edges, etc.) of the forming crystals. The molecular differences between the samples direct the above phase transition into various directions (fourth-degree specificity). This method detects the joint manifestation in the tear of many changes brought by a neurodegeneration of the brain. Above all, our purpose was to predict neurodegenerative diseases (neurocognitive disorders of the Alzheimer's disease spectrum, especially Alzheimer's disease), and/or quickly and accessibly detect them for those affected.

Figure 2:
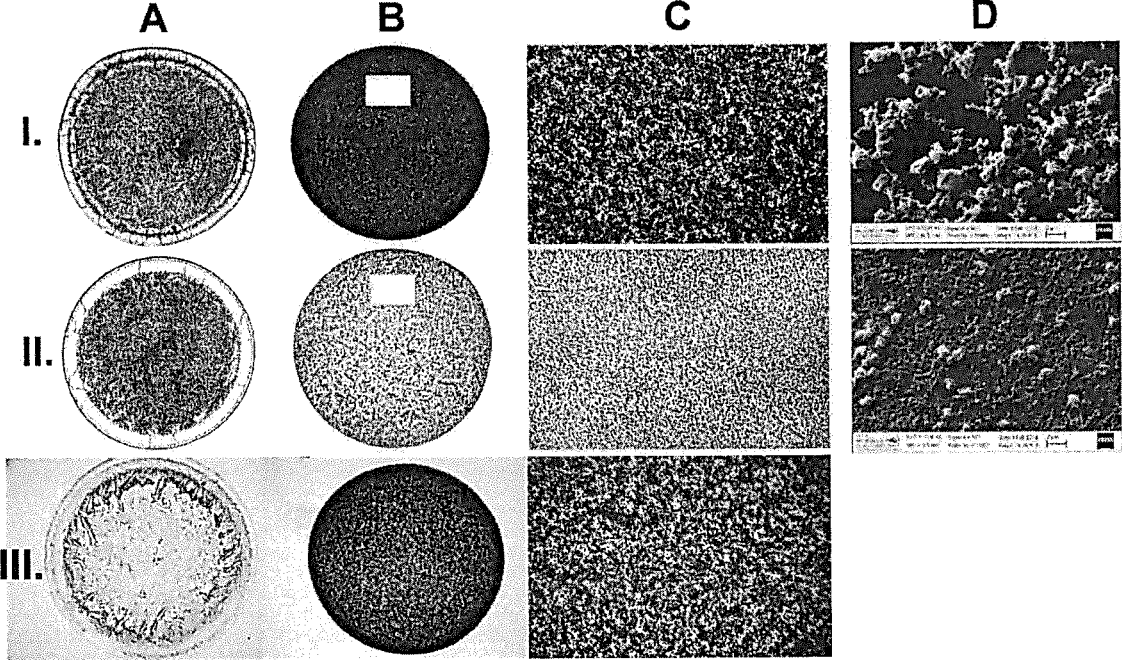
FIG. 2 shows dried native tear sample patterns (A), and dried tear sample patterns created by a solution of the invention (also referred to as "L-AD solution") (B, C, D) for elderly control individual (1) and for patient with Alzheimer's disease (11), in images taken using optical microscope (A, B: 64×; C: 320×) and scanning electron microscope (D; 4.00 K×) (own photographs). Line III shows raw images of dried teardrops (A: native, magnification: 64×; B: treated with L-AD solution, magnification: 64×; C: treated with L-AD solution, magnification: 320×) (own photographs). In column D, the scalebar is 2 μm.

On the basis of the results of the L-AD test, the sample profile of the patients without neurocognitive disorder of the Alzheimer's disease spectrum and that of the patients characterisable with a neurocognitive disorder of the Alzheimer's disease spectrum can be distinguished to a significant extent. In the case of tear samples treated with L-AD solution and dried, the particles constituting the pattern of the dried sample, the crystals, crystal structures formed as a single block show different patterns for patients without neurocognitive disorder of the AD spectrum and for patients characterisable with a neurocognitive disorder of the AD spectrum. On the contrary, native dried samples do not show differences of diagnostic relevance between patients without neurocognitive disorder of the AD spectrum and patients characterisable with a neurocognitive disorder of the AD spectrum. Column A of FIG. 2 shows native dried tear samples: sample I-A is a sample of an individual without cognitive deficit, and sample II-A is a sample of a patient with a neurocognitive disorder of the Alzheimer's disease spectrum. It can be observed that the patterns of the two dried tear samples are not different from each other to a diagnostically relevant degree.

However, the dried tear samples of the invention show—also by microscopy (e.g. optical microscope or electron microscope)—that in the case of patients characterisable with a neurocognitive disorder of the Alzheimer's disease spectrum the dried tear samples of the invention are paler in terms of density and its particle range is smaller as compared to the dried tear samples of the invention for patients showing no cognitive deficits. Columns B to D of FIG. 2 show dried tear samples of the invention. The figures of Lines I show a sample of an individual showing no cognitive deficit, and those of Line II show a sample of a patient characterisable with a neurocognitive disorder of the Alzheimer's disease spectrum. The images of columns B and C were created using light microscope at a magnification of 64× and 320×, respectively. Column C shows magnified images of the area marked in white in the images of column B. Column D shows images created using scanning electron microscope. The pattern differences between the images of columns B to D of Line I (sample of an individual showing no cognitive deficit) and columns B to D of Line II (sample of a patient characterisable with a neurocognitive disorder of the Alzheimer's disease spectrum) are clearly visible.

The observable particles (peptide or protein agglomerates, and the images thereof) are larger in size and more densely dispersed in the images of Line I, and are smaller in size and more sparsely dispersed in Line II. Based on the above differences, a) a conclusion can be made as to whether a patient is at risk of or suffers from a neurocognitive disorder of the Alzheimer's disease spectrum (that is, a prediction or diagnosis can be provided in relation to the neurocognitive disorder of the Alzheimer's disease spectrum); and/or b) the status of a patient can be monitored in relation to the risk of a neurocognitive disorder of the Alzheimer's disease spectrum, or in relation to a neurocognitive disorder of the Alzheimer's disease spectrum.

Hence, the method of the invention (alternative references: "L-AD diagnostic test", or "LacrimAD test", or "L-AD test") can successfully differentiate patients characterisable with a neurocognitive disorder of the AD spectrum, especially patients with Alzheimer's disease, from control individuals adjusted for elderly age and for gender. The L-AD diagnostic test is simple, quick (sample processing and evaluation takes only 30 minutes), cost-effective (with an estimated total cost of HUF 10000/person/sample), and non-invasive. Upon interacting with the tear sample normalised for protein amount, the reagent of unique composition according to the invention (L-AD solution) is able to detect differences of diagnostic power between healthy individuals and patients characterisable with a neurocognitive disorder of the AD spectrum, especially Alzheimer's disease, at a sufficiently high specificity and sensitivity.

Thus, the invention also relates to a method for predicting and/or diagnosing and/or monitoring a neurocognitive disorder of the Alzheimer's disease spectrum in a patient, the method comprising:

(a) normalising a tear sample from the patient for protein concentration;

(b) contacting, preferably mixing, the normalised tear sample with a solution of the invention;

(c) applying an amount of the contacted normalised tear sample, preferably an amount of about 1 μL, to a surface, preferably a hydrophobic plastic surface;

(d) allowing the applied tear sample to dry;

(e) drawing a conclusion on the basis of the pattern of the dried tear sample or on the basis of the pattern of an image of the dried tear sample as to whether the patient is at risk of or suffers from a neurocognitive disorder of the Alzheimer's disease spectrum.

The conclusion based on the pattern is typically a conclusion based on the average particle size and/or particle density of the particles constituting the pattern of the dried tear sample, and the average particle size and particle density are typically examined using microscope, at room temperature, e.g. at a temperature of 24° C. to 25° C. The dried tear sample is round-shaped and, when 1 μL of the contacted normalised tear sample is applied to the surface, has a typical diameter of about 0.9 to 1.3 mm, optimally about 1.1 mm.

In an embodiment of the invention, the method for predicting or diagnosing or monitoring a neurocognitive disorder of the Alzheimer's disease spectrum comprises taking an image, e.g. a digital photograph, of one or more tear samples contacted with an L-AD solution and dried (i.e. dried tear samples according to the invention), optionally using a microscope, preferably an optical microscope.

In an embodiment of the invention, an overview image of the dried tear sample, preferably of a rectangular shape, is also made, e.g. using a magnification of 64×, and/or a high-resolution image, e.g. using a magnification of 320×. Optionally, the overview image is taken of the visual field of the microscope, and the high-resolution image is preferably taken of an area of the overview image or of the visual field of the microscope where the pattern shows the highest reproducibility and the lowest diversity. In a preferred embodiment of the invention, in the case of an overview image or microscope visual field with a shape of a circular disk, the high-resolution image is taken at half of the radius of the circular disk. If a carrier with a hydrophobic plastic surface is used when drying the tear sample, then the stagogram will be ringless and completely homogeneous enabling making an image of any part thereof within the limits of the stagogram.

Optionally, one or more image transformation steps enabling image processing, e.g. binary conversation, is also carried out. Optionally, the image is subjected to graphical conversion, e.g. a two-colour graphical conversion, e.g. black-and-white graphical conversion. "Colour" refers to dense colours and/or patterns. "Two-colour graphical conversion" refers to converting the relevant information of the image into two colours. The skilled person may carry out the graphical conversion using a computer software program, a number of options are available, e.g. Photoshop.

In a preferred embodiment of the invention, one or more values are calculated for the dried tear sample on the basis of the image obtained by optical microscope, optionally on the basis of the image generated (obtained) by image transformation step(s), e.g. graphical conversion, via analysis (e.g. manually; using an image analysing computer software program, e.g. ImageJ), said one or more values are selected from:

(i) the number of particles in the sample area, that is, particle count;

(ii) the sample area covered by particles expressed, for example, in $\mu m^2$; and (iii) the average size of the particles expressed, for example, in $\mu m^2$, which is the ratio between value (ii) and value (i) (i.e. the sample area covered by particles divided by the number of particles in the sample area), or in other words (and hereinafter), the area/particle ratio (or area/particle count ratio);

wherein the term "sample area" refers to the examined part of the visual field of the microscope or to the examined part of the image taken (made) of the visual field of the microscope.

In the context of the images, "particle" refers to the notion according to the general understanding in the field, that is, an image-part that can be considered as one unit definable by its contour and/or shade is considered as one particle. Typically, particles are of varied shape. Thus, each particle in the image corresponds to one particle contributing to the pattern of the dried tear sample.

In a preferred embodiment of the invention, one or more of (i) the particle count, (ii) the value of the sample area covered by particles, and (iii) the area/particle count ratio [the ratio of (ii) to (i)] is compared with the corresponding reference value(s), and on the basis of such comparison a) a conclusion is made as to whether the patient is at risk of or suffers from a neurocognitive disorder of the Alzheimer's disease spectrum (that is, a prediction or diagnosis is made in relation to a neurocognitive disorder of the Alzheimer's disease spectrum); and/or b) the status of the patient is monitored in relation to the risk of a neurocognitive disorder of the Alzheimer's disease spectrum, or in relation to a neurocognitive disorder of the Alzheimer's disease spectrum.

According to a preferred embodiment of the invention, in relation to the patient giving the tear sample, a diagnostic value (DV) is derived from the area/particle ratio using the following formula:

$$DV[\%] = (P_{(area/particle\ ratio)}/Control_{(area/particle\ ratio)}) \times 100$$

wherein $P_{(area/particle\ ratio)}$ is the value of the area/particle ratio determined from a dried tear sample according to the invention of the patient, $Control_{(area/particle\ ratio)}$ is the arithmetic average of area/particle ratio values determined from dried tear samples according to the invention of patients with a known diagnosis of not having (not showing) neurocognitive disorder of the AD spectrum, and then the DV value thus obtained is compared with one or more reference values, and on the basis of said comparison of the DV value with the one or more reference values a) a conclusion is made as to whether the patient is at risk of or suffers from a neurocognitive disorder of the Alzheimer's disease spectrum (that is, a prediction or diagnosis is made in relation to the neurocognitive disorder of the Alzheimer's disease spectrum); and/or b) the status (condition) of the patient is monitored in relation to the risk of a neurocognitive disorder of the Alzheimer's disease spectrum, or in relation to a neurocognitive disorder of the Alzheimer's disease spectrum.

When carrying out the invention, the $Control_{(area/particle\ ratio)}$ value can be determined on the basis of the present description, or a value optionally already available can be used. Whichever option is used, the conditions of determining $P_{(area/particle\ ratio)}$ and $Control_{(area/particle\ ratio)}$ must be such as to enable comparison. Thus, the determination of $P_{(area/particle\ ratio)}$ and $Control_{(area/particle\ ratio)}$ is carried out using tear samples normalised for the same protein concentration, and using L-AD solutions of the same composition, furthermore the ratio between the volume of the normalised tear sample and the volume of the solution of the invention contacted (preferably mixed) with the former is constant, as are the volume of the contacted normalised tear sample applied to the surface and the wettability of the carrier applied. Furthermore, preferably identical microscope and camera systems are used but it is not necessary. In case of using a new detection system (microscope and camera), new photos of the control (reference) stagograms must be taken as reference samples. In case only digital comparison is carried out, the pixel numbers of the images must be increased or reduced according to the ratio between the magnification of the new microscope objective and the magnification of the old microscope objective (in line with the new requirements). The image analysis software programs must use the same algorithms for digital image scaling, graphical conversion, pixel colour scale range (e.g. 8- or 16-bit), and black-and-white pixel identification to ensure interchangeability. Several programs comply with the international standards for these parameters (e.g. Photo-Shop, ViewNX-Nikon, ImageJ etc.).

The reference value is determined using patients with a known diagnosis of not having (showing) neurocognitive disorder of the AD spectrum and their data, and patients known to have a neurocognitive disorder of the Alzheimer's disease spectrum (e.g. MCD patients, AD patients) and their data, and considering medical ethics.

In a preferred embodiment of the invention, the DV [%] value is compared with an RV [%] reference value. The RV [%] value can be determined as follows.

The values of the area/particle ratio are determined using the L-AD method for patients characterisable with a neurocognitive disorder of the AD spectrum and for patients showing no neurocognitive disorder of the AD spectrum. A value for each patient is calculated from the value of the area/particle ratio of the patient thus obtained, using the following formula, which is analogous to the above formula:

$$V[\%] = (P_{(area/particle\ ratio)}/Control_{(area/particle\ ratio)}) \times 100$$

wherein $P_{(area/particle\ ratio)}$ is the value of the area/particle ratio determined from a dried tear sample according to the invention of a patient identified as a patient characterisable with a neurocognitive disorder of the Alzheimer's disease spectrum using a known diagnostic method, $Control_{(area/particle\ ratio)}$ is the arithmetic average of area/particle ratio values determined from dried tear samples according to the invention of a group of individuals with a known diagnosis of showing no neurocognitive disorder of the AD spectrum.

The above formula is fittingly applied when the goal is to determine the value of V and RV for patients showing any neurocognitive disorder of the AD spectrum. For example, if the goal is to determine the value of RV for Alzheimer's disease, then the value of V is calculated by substituting the numerator of the fraction in the formula of V with the value of the area/particle ratio determined from a dried tear sample according to the invention of a patient identified as being a patient characterisable with Alzheimer's disease using a known diagnostic method (that is, other than the method of the invention).

In line with the above, and in compliance with medical considerations and medical ethics, the V values obtained for the individual patients are used to determine the numerical value of RV [%] for a neurocognitive disorder of the Alzheimer's disease spectrum, e.g. Alzheimer's disease or MCD.

In a preferred embodiment of the invention, the RV [%] value for the presence of MCD or for the risk of Alzheimer's disease is 50% or is less than 50%. In a preferred embodiment of the invention, the RV [%] value for Alzheimer's disease is 5% or is less than 5%.

In a preferred embodiment of the invention, a DV [%] value of not higher than 50% and higher than 5% for a patient leads to the conclusion that the patient is having a mild cognitive disorder (MCD) or is at risk of Alzheimer's disease. In a preferred embodiment of the invention, a DV [%] value of 5% or lower than 5% for a patient leads to the conclusion that the patient has Alzheimer's disease.

When carrying out the invention, the RV [%] value can be determined on the basis of the above, or a value optionally already available can also be used. Whichever option is used, when the values of DV [%] and RV [%] are determined, the conditions must be such as to enable comparison. The determination of the values of DV [%] and RV [%] is carried out using tear samples normalised for the same protein concentration, and using L-AD solutions of the same composition, furthermore the ratio between the volume of the normalised tear sample and the volume of the solution of the invention contacted (preferably mixed) with the former is constant, as are the volume of the contacted normalised tear sample applied to the surface and the wettability of the carrier applied. Furthermore, preferably identical microscope and camera systems are used but it is not necessary. In case of using a new detection system (microscope and camera), new photos of the control (reference) stagograms must be taken as reference samples. In case only digital comparison is carried out, the pixel numbers of the images must be increased or reduced according to the ratio between the magnification of the new microscope objective and the magnification of the old microscope objective (in line with the new requirements). The image analysis software programs must use the same algorithms for digital image scaling, graphical conversion, pixel colour scale range (e.g. 8- or 16-bit), and black-and-white pixel identification to ensure interchangeability. Several programs comply with the international standards for these parameters (e.g. Photo-Shop, ViewNX-Nikon, ImageJ etc.).

In an embodiment of the invention, standard statistical methods (one-way ANOVA Bonferroni, $p^{***}<0.001$) are used to compare the area/particle ratio of the gender- and age-adjusted group of patients without cognitive deficits (control group) and the area/particle ratio of the group of patients with a neurocognitive disorder of the Alzheimer's disease spectrum.

Preferably, the diagnostic method of the invention is used in a patient without none of the following conditions:

post-operative condition after an eye surgery; post-operative condition after an intervention directly affecting the flow and/or metabolism of the tear; post-operative condition after a surgery affecting lacrimal canal or lacrimal gland; a disease of the lacrimal canal;

those inflammatory and immunological processes, auto-immune diseases, viral infections and bacterial infections which primarily affect the eyes and the lacrimal glands and influence the sensitivity and validity of the L-AD test.

Of course, the diagnostic method of the invention cannot and does not aim to replace the complex medical task that is a synthesis of the results of the clinical anamnesis, laboratory tests, neurological, psychiatric and physical examinations, cognitive tests, and brain imaging (CT, MR) examinations. However, the use of the method of the invention can facilitate the medical diagnostic work and can replace other expensive or painful examinations (e.g. lumbar puncture, brain PET) as it is simple, quick, easily available, painless, and cost-effective. Similarly to the above-mentioned examinations, the method of the invention, i.e. LacrimAD laboratory diagnostic method developed by us can help clinicians in making a probability clinical diagnosis of a neurocognitive disorder of the Alzheimer's disease spectrum, especially Alzheimer's disease, and to make a more accurate diagnosis of MCD than before.

Table 1 compares the characteristics of the tests used in the diagnostics of neurocognitive disorders of the AD spectrum such as Alzheimer's disease with the characteristics of the method of the invention.

TABLE 1 characteristics of the tests used in the diagnostics of neurocognitive disorders of the AD spectrum such as Alzheimer's disease

| Test | Invasivity | Pain | Sensitivity | Cost/capital (HUF) | Comment |
|---|---|---|---|---|---|
| Cranial CT | — | + | + | 43000 | Used in routine |
| Cranial MR | | + | +++ | 84000 | diagnostics |
| Brain SPECT | — | + | ++ | 51000 | |
| FDG PET | — | + | ++++ | 240000 | No health insurance coverage in dementia |
| Amyloid PET | — | + | +++++ | 900000 | Only used in studies but not in routine diagnostics |
| Tau PET | — | + | +++++ | 900000 | scientific clinical |
| Liquor biomarkers | +++ | +++ | ++++ | 20000 | Use in routine diagnostics is limited at the moment |
| Plasma biomarkers | ++ | + | ++++ | 18000 | Validation in progress |
| LacrimAD tear test | — | — | at least ++++ | 10000 | Validation in progress |

Such novel analysis of the tear is useful in the diagnostic screening of a very large population, and in helping the clinical diagnosis of neurocognitive disorders of the Alzheimer's disease spectrum (AD spectrum neurocognitive disorders) including the genetic forms of Alzheimer's disease, Down's syndrome depending on age, isolated and combined cerebral amyloidopathies, tauopathies, the combined manifestation of Alzheimer's disease with type II diabetes mellitus, and the manifestation of mild cognitive disorder (MCD) related to Alzheimer's disease, especially Alzheimer's disease. From the viewpoint of the patient, one great advantage is that the method is non-invasive and painless.

EXAMPLES

Example 1

Preparation of the LacrimAD solution $AuCl_3 \times 2H_2O$ with an $Au^{3+}$ content of 57% and with a 40% compensation based on MW was dissolved in distilled water to obtain a solution with an $Au^{3+}$ concentration of 2 mM (9.5 mg salt/10 mL). Part of the solution was divided into 50-mL aliquots, which were frozen at a temperature of −20° C., then thawed, and the preparation of the solution proceeded according to Example 1A. The remainder of the solution was not frozen, and the preparation of the solution proceeded according to Example 1B.

Example 1A

The frozen solution according to Example 1 was thawed, and then filtered through a filter with a pore size of 0.45 μm. To 500 μL of the solution thus obtained, 499.1 μL of distilled water was added. To the solution thus obtained, 0.4 μL of a ZnCl$_2$ stock solution (50 mM; 6.815 mg salt/mL) was added, followed by the addition of 0.8 µL of a AgNO$_3$ stock solution (50 mM; 8.494 mg salt/mL), and the solution thus obtained was finally vortexed (300 rpm/30 sec.), and stored at room temperature.

Ion concentrations of the solution thus obtained:

Au$^{3+}$ concentration: 1 mM,

Zn$^{2+}$ concentration: 20 µM,

Ag$^+$ concentration: 40 µM.

The solution was vortexed before diagnostic use.

Example 1B

The non-frozen solution according to Example 1 was filtered through a filter with a pore size of 0.45 µm, and to 500 µL of the solution thus obtained, 499.1 µL of distilled water was added. To the solution thus obtained, 0.4 µL of a ZnCl$_2$ stock solution (50 mM; 6.815 mg/mL), followed by the addition of 0.8 µL of a AgNO$_3$ stock solution (50 mM; 8.494 mg/mL), and the solution thus obtained was finally vortexed (300 rpm/30 sec.), and stored at room temperature. Ion concentrations of the solution thus obtained:

Au$^{3+}$ concentration: 1 mM,

Zn$^{2+}$ concentration: 20 µM,

Ag$^+$ concentration: 40 µM.

The solution was vortexed before diagnostic use.

Example 2

At the Memory Ambulance of the Psychiatric Clinic of the Faculty of General Medicine of the University of Szeged (SZTE), tear samples from 159 patients (n=159) with an AD diagnosis made on the basis of the DSM-5 [American Psychiatric Association, (2013) and NINCDS-ADRDA (Mc-Khann, 1984] criteria (AD group) were taken upon written consents (Ethics Approval Nos.: SZTE, 3543/2015; 93/2018-SZTE/4263; 152/2018-SZTE/4356). 10 patients characterisable with a mild cognitive disorder were also enrolled in the study; these patients had an MCD diagnosis made on the basis of the test used for patients with Alzheimer's disease (MCD group, n=10). As controls (n=80), gender- and age-adjusted individuals not showing cognitive deficits were invited to participate in the study (control group). To ensure specificity, individuals with Down's syndrome without Alzheimer's disease (n=8) (Down group) and individuals with Parkinson's disease (n=25) (Parkinson group) were also enrolled. Individuals with a neurocognitive disorder not associated with AD, as well as those with an eye surgery during a 10-year period preceding the study and those affected by a diagnosed ophthalmological pathology or a pathology affecting the surface of the eyes were excluded from the study.

The tests were conducted using both fresh and frozen tear samples. It was concluded that freezing (at –20° C.) does not affect the sensitivity indicators of the test. Upon determining the protein content, thawed samples were treated and measured at a standardized protein concentration.

During the study, tear samples treated with the L-AD solution of Example 1A and Example 1B, resp. were used.

During the preliminary experiments conducted in preparation of the study, two types of teardrops (tear samples) applied to and dried on special hydrophobic plastic surfaces were examined (FIG. 2): native complete samples (FIG. 2/I-II-A; magnification: 64×) and samples treated with the L-AD solution. In the case of the drops treated with the L-AD solution, both the total area (FIG. 2/I-II-B; magnification: 64×) and the areas within the drop were examined (FIG. 2/I-II-C; magnification: 320×).

Figures 5, 6:
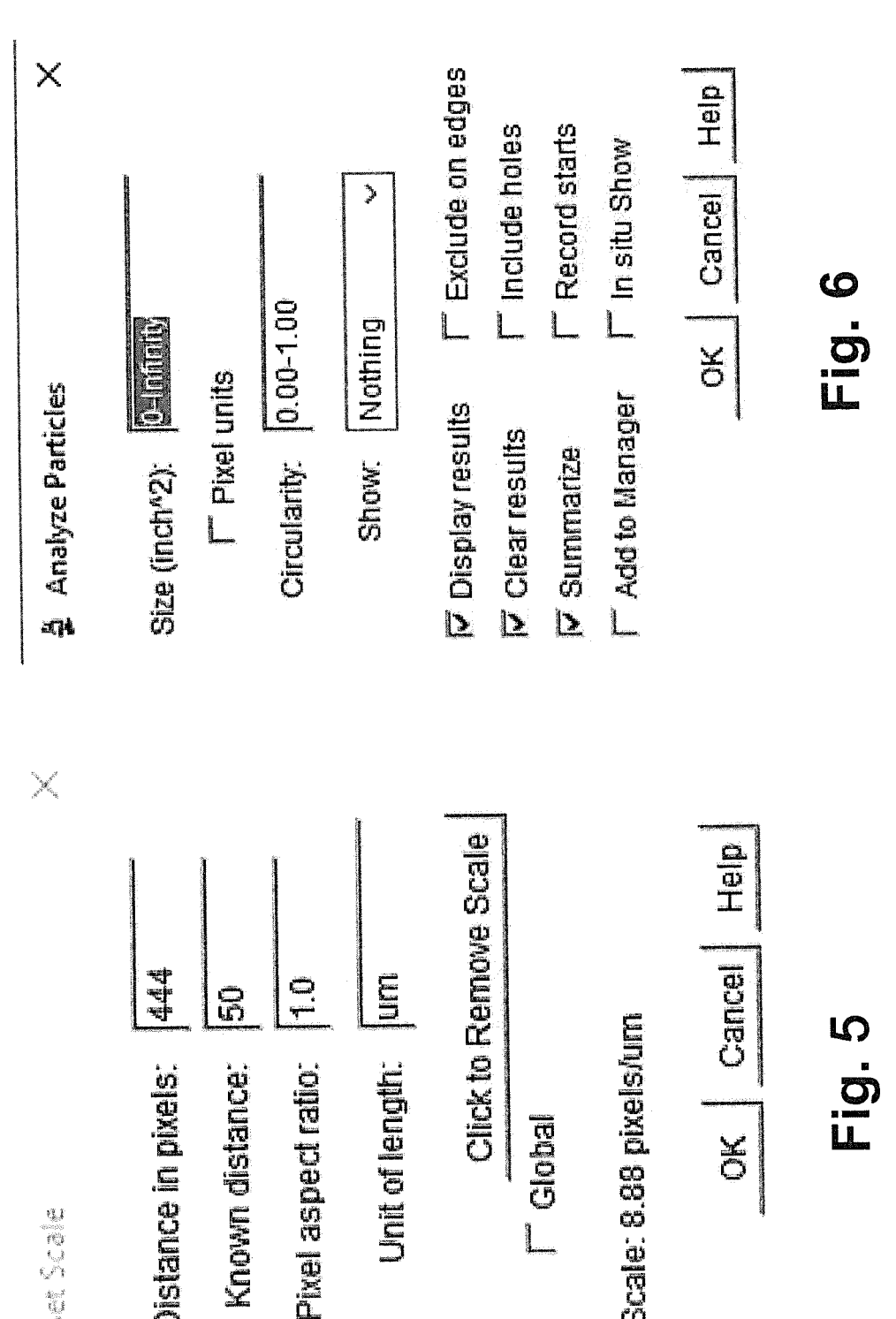
FIGS. 5 and 6 show the program settings of the ImageJ program used in Example 2.

Tests were conducted using an optical microscope and a DSLR camera. The graphical conversion was carried out by the consecutive use of various digital image analysis programs (ViewNX2, Photoshop, and ImageJ). These programs are commercially available, and are suitable for the present purposes. Image processing involved the following steps:

a. Technical Background of the Photograph Taken
   i. Microscope objectives: Leitz Wetzlar
      1. 160/-, EP, 132/0.40 PHACQ1
      2. 160/-, PL, FLUOTAR, 6.3/0.20; about 90-95 grid/mm resolution
   ii. Spacer (light path): PERIPLAN 10×18, TL160 mm
   iii. magnification of 320×, rectangle
b. Primary (raw) photograph: RAW/MC/8 bit/minimum 16 MP (Nikon NEF); ISO 100; 1/160 shutter speeds; ~40.000 Lux
c. WewNX2 (Nikon)
   i. Opened using the program ViewNX2
   ii. Edit→Sharpness 1→Contrast 1→D-Lightening HS 1→Nature→Save
   iii. Convert file→TIFF (8 bit)→LZV compression
d. Photoshop CS3 (or CC)
   i. TIFF opened using the program Photoshop CS3 (or CC)
   ii. Colour mode (image)→devignetting (correction: midtone, exp. 15%, paintbrush mode: 1400)→grayscale
   iii. Image→Corrections→Exposure→parameters:

| Exposure | +1 |
| Offset | −0.2 |
| Gamma correction | 0.75 (→) | iv. Filter→Sharpening→Blur mode→parameters:

| Amount | 150 |
| Radius | 0.5 |
| Threshold | 0 | v. Foreground colour: white (#ffffff) (L100/RGB:255)
   vi. Background colour: white (#ffffff) (L100/RGB:255)
   vii. Filter→Artistic→Stamp (sketch)→parameters:

| Light/dark balance | 10 |
| Smoothness | 1 | viii. Saving done (TIFF, interlacing, LZW)
e. ImageJ
   i. The graphical TIFF generated as a result of step d. was opened in ImageJ.
   ii. Analyze→set scale:
      Settings (see FIG. 5):
         distance in pixels: 444
         known distance: 50 µm
         scale: 8.88 pixeVpm
      The area to be measured was marked
      Analysis (see FIG. 6): Analyze→Analyze particle
         Detailed data from the 'Results' window and summary results from the 'Summary' window [values from the "Count" (number of particles) column, the "Total area" (sample area covered by particles) column, and the "Average size"

(area/particle ratio) column] were copied into a separate Excel file. The "Summary" window is generated by the software. The number in the "Average size" column of the "Summary" window is the number expressing the area/particle ratio.

Quantitative data from the digital photographs (optionally 16 megapixel in the present case) were also analysed.

During the preliminary experiments conducted in preparation of the study, the analyses covered, among others, the ratio between the areas of coverage of the two colours in the black-and-white pattern of the graphical conversion, and the particle count and particle size data.

Figure 3:
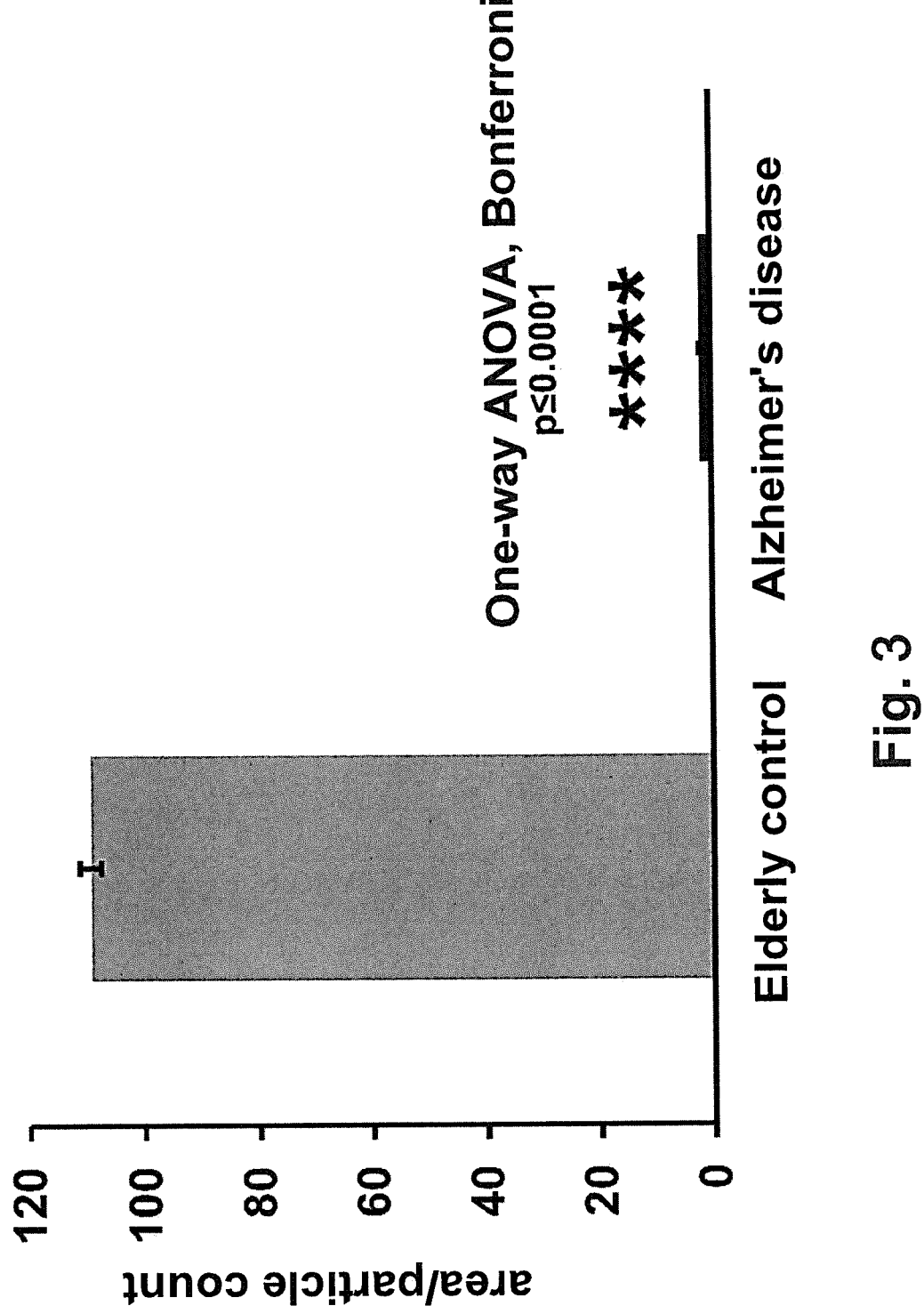
FIG. 3 shows a quantitative comparison of dried tear samples of the control group and of the group of patients with Alzheimer's disease on the basis of data derived from the photographs of dried tear samples taken by optical microscope, more specifically from the ratio between the sample area covered by particles and the number of particles, as described in Example 2.
Figure 4:
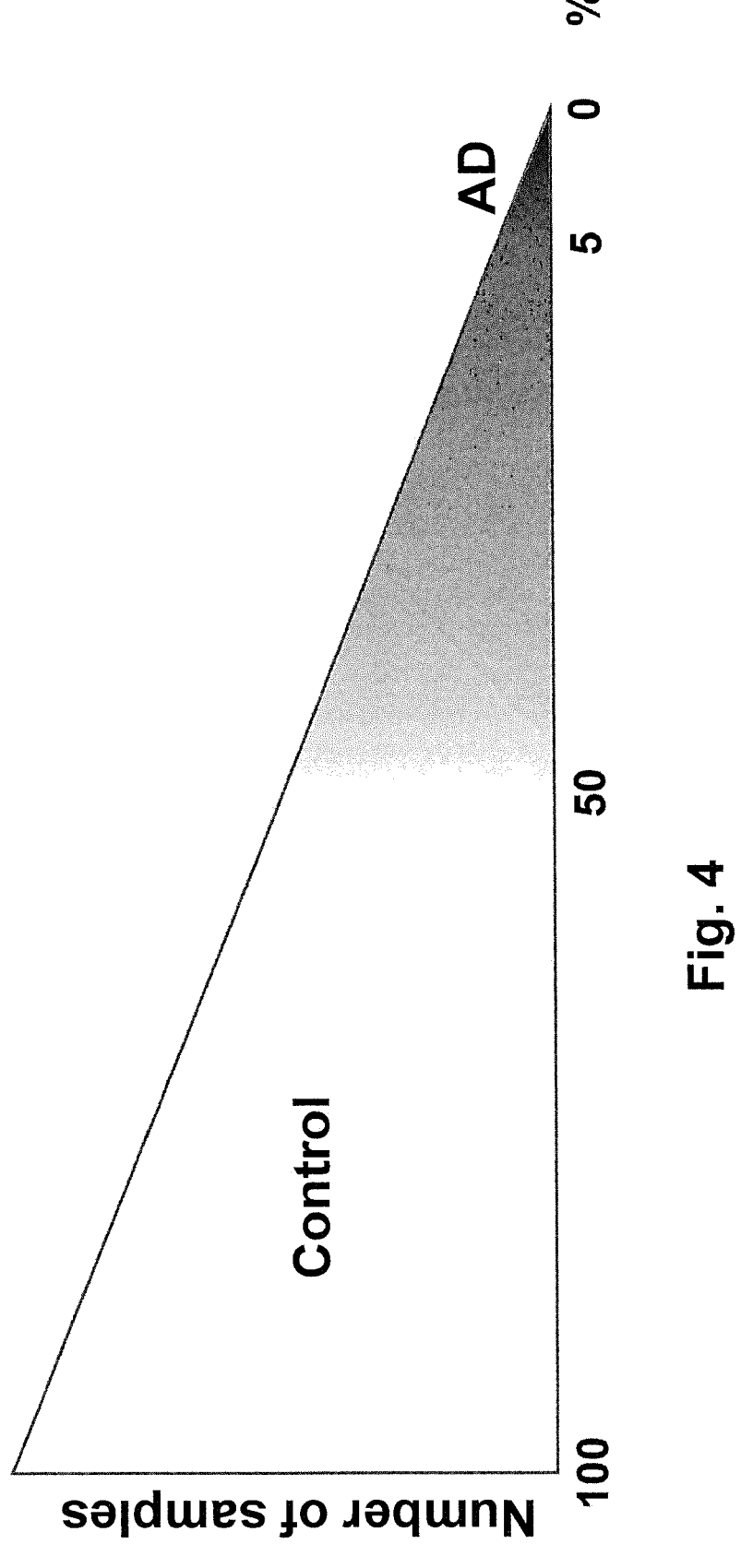
FIG. 4 demonstrates that at the case numbers processed so far, Alzheimer's disease is unambiguous and can be concluded for the samples with a low density (DV≤5%). At the case numbers processed so far, all other samples should be considered as non-Alzheimer samples in terms of safety and healthcare ethics, especially those above 50%.

The analyses also covered the data for the particle count, for the sample area covered by particles, and for the area/particle count. FIG. 3 demonstrates the comparison of the area/particle count ratios of the control patients with those of the patients with Alzheimer's disease.

Figure 7:
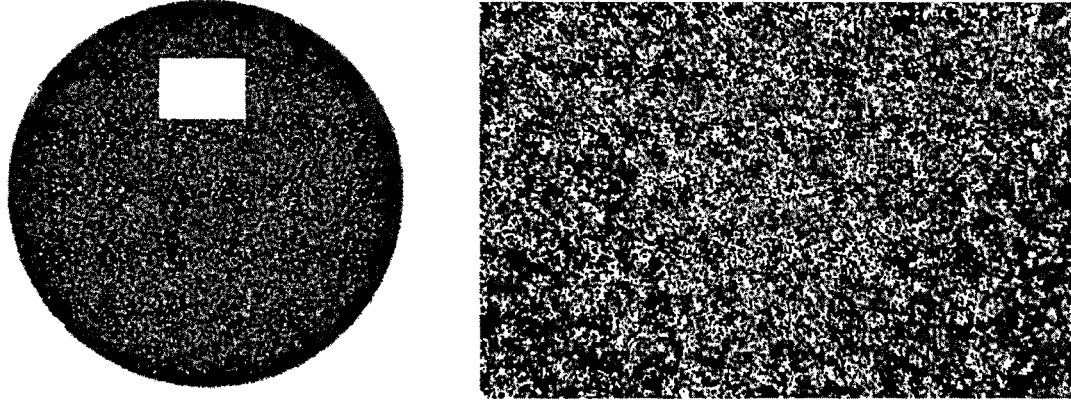
FIG. 7 shows the analysis of data from 2 patients using ImageJ on the basis of possible exemplary data of the study described in Example 2. Legend: Slice: assessed image; Count: number of particles in the sample area; Total Area: sample area covered by particles; Average Size: the average size of the particles (area/particle ratio); % Area: percentage of the sample area covered by particles in the total sample area; Non-AD: data series of a patient not characterisable with neurocognitive disorder of the Alzheimer's disease spectrum; AD: data series of a patient with Alzheimer's disease; Control: value of the Control according to the number of cases processed in Example 2; V: L-AD diagnostic value calculated for patient with known diagnosis.

In order to prepare the % graduation of the diagnostic scale, the value of RV was determined as follows:

(1) For AD Patients:

with the use of the formula $V=(P_{(area/particle\ ratio)}/Control_{(area/particle\ ratio)})\times100$, a value was calculated for each patient known to have AD and enrolled in the study via substituting the numerator of the fraction in the formula with the value of the area/particle ratio of the given AD patient, and substituting the denominator of said fraction with the arithmetic average of the values of the area/particle ratios of the patients in the control group. (See FIG. 7, for example)

(2) For MCD Patients:

with the use of the formula $V=(P_{(area/particle\ ratio)}/Control_{(area/particle\ ratio)})\times100$, a value was calculated for each patient known to have MCD and enrolled in the study via substituting the numerator of the fraction in the formula with the value of the area/particle ratio of the given MCD patient, and substituting the denominator of said fraction with the arithmetic average of the values of the area/particle ratios of the patients in the control group.

The $Control_{(area/particle\ ratio)}$ data according to the number of cases processed so far 109.264+/−1.8879 (SEM), wherein SEM=SD/$\sqrt{n}$ (the quotient of the standard deviation and the square root of the case number).

Next, a statistical analysis was carried out (one-way ANOVA Bonferroni, $p^{***}<0.001$).

On the basis of the case numbers processed so far, the values of RV for AD and MVD were 5% and 50%, respectively.

In order to provide a diagnostic classification of the individual patients according to L-AD test, the value calculated above for each patient was compared with the RV value. The status of the patient was classified as follows:

when V≤5%, it was concluded that the L-AD test classifies the patient as a patient with Alzheimer's disease, when 5%<V≤50%, it was concluded that the L-AD test classifies the patient as a patient with MCD, when V>50%, it was concluded that the L-AD test classifies the patient as a patient showing neither Alzheimer's disease nor MCD.

The results thus obtained were compared with the previously made diagnoses of the patients. In case the result of the L-AD test was in agreement with the known diagnosis, the result of the L-AD test of the patient was qualified as a true positive (in case of AD patient) or a true negative (in case of patient not showing cognitive deficits). In case the result of the L-AD test classified a patient known to be not showing cognitive deficits as a patient with AD, then the result of the L-AD test was qualified as a false positive. In case the result of the L-AD test classified a patient known to have AD as a patient without Alzheimer's disease or MCD, then the result of the L-AD test was qualified as a false negative. The results are presented in a tabulated form (see Table 2).

On the basis of the results of the L-AD test, it was found that the sample profile of the control group and that of the AD group are distinguishable to a significant degree. Under an optical microscope, the AD samples are paler in terms of density, and their particle size ranges are smaller than those of the controls. The data were also examined using scanning electron microscope to qualitatively and visually differentiate the structuredness of the complexes formed by the components of the L-AD solution and of the teardrop (FIG. 2/I-II-D; magnification: 4.00K×).

The quantitative analysis of the results of the L-AD test was carried out upon normalisation for age and gender.

In order to determine specificity and sensitivity, our results were also compared with other diseases, such as with the L-AD-specific stagograms of individuals with Parkinson's disease and of individuals with Down's syndrome without Alzheimer's disease.

TABLE 2

Assessment of the diagnostic specificity and sensitivity of LacrimAD in AD and in other neuropsychiatric diseases

|  | True positive | True negative | False positive | False negative | Specificity | Sensitivity |
|---|---|---|---|---|---|---|
| EC | — | 62 | 18 | — | 77.5% | — |
| PD | — | 18 | 7 | — | 72% |  |
| DS | — | 5 | 3 | — | 62.5% |  |
| AD | 138 | — | — | 21 | — | 88% |

EC=elderly control; PD=Parkinson's disease; DS=Down's syndrome without Alzheimers disease condition; AD=Alzheimers disease; True positive=agreement between the L-AD test and the AD diagnosis; True negative=control individuals showed control values also in the L-AD test; False positive=a control, PD, or DS patient showing a pattern corresponding to AD patient; False negative=AD patient showing a pattern corresponding to control.

Below is a description of the detailed conditions of the experiments and assessments pertaining to the above.

TABLE 3

Laboratory consumables and chemicals used

| Description | Catalogue No. | Manufacturer/ Distributor |
|---|---|---|
| Gold chloride ($AuCl_3 * _2H_2O$) (MW = 339.36 g/mol) | A-260 (57% Au) | Reanal |
| Zinc chloride (MW = 136.3 g/mol) | 96468-50g | FLUKA/BioChemica |
| Silver nitrate (MW = 169.88 g/mol) | 03090-101-160 | Molar Chemicals Kft. |
| Puradisc 25 AS25 0.45pm sterile filter | 514-8021 | VWR International Kft. |
| Glass capillary, 1.2 mm OD, 0.69 mm ID, 100 mm | 300044 | CEBIO |
| Petri dish (90 × 14.2 mm) | 90-190 | BIOLAB Zrt. |
| UltraPure Dnase/Rnase-free distilled water | 10977035 | Life Technologies Inc. |
| 0.1-10 μL pipette tips of Biosphere plus quality, neutral, boxed | 70.1130.200 | Sarstedt Kft. |

TABLE 3-continued

Laboratory consumables and chemicals used

| Description | Catalogue No. | Manufacturer/ Distributor |
|---|---|---|
| 20-200 μL pipette tips of Biosphere plus quality, neutral, boxed | 70.1130.202 | Sarstedt Kft. |
| Parafilm | WS-5000-10 | Izinta |
| 96-well plate half area | CLS3695-100EA | Biocenter Kft. |
| 4,4'-Dianilino-1,1'-binaphthyl-5,5'-disulfonic acid dipotassium salt | D4162-5MG | Sigma Aldrich © |
| SmartPak ® DQ3 Purification Pack | SPR00SIA1 | MERCK |
| Centrifuge tube with inner plug cap (15 mL) | 734-1862 | VWR International Kft. |
| 2 mL PP Eppendorf | 3-204-85-0 | Biocenter |
| 0.2 mL PCR tube | AB-0620 | Biocenter |
| Essential oil mixture for air purification | | Aromax Natural Products |
| Ethanol 96% | 02911-469-430 | Molar Chemicals Kft. |

Laboratory Devices Used:
1. Tabletop centrifuge (300 g);
2. Manual pipettes (0.1 to 3 μL; 0.5 to 10 μL, 2 to 20 μL, 20 to 200 μL);
3. Fluorescent plate reader (e.g. BMG NOVOStar);
4. Normal transmission microscope;
5. DSLR camera (min. 16 MP, DX);

Preparation of the Applied L-AD Solution
1. $AuCl_3 \times 2H_2O$, minimum $Au^{3+}$ content: 57%, compensation: 40% (based on the MW);
2. This was dissolved in distilled water to obtain a solution of 2 mM.
3. The Au solutions were divided into aliquots of 50 mL each and were frozen at −20° C.;
4. Composition of the L-AD solution, and dissolution order
   a. 500 μL $Au^{3+}$ solution (2 mM)
   b. +499.1 μL distilled water (final $Au^{3+}$ concentration: 1 mM)
   c. +0.4 μL $ZnCl_2$ solution (stock solution: 6.815 mg/50 mM/mL), final concentration: 20 μM;
   d. 5-minute incubation+vortexing twice;
   e. +0.8 μL $AgNO_3$ solution (stock solution: 8.494 mg/50 mM/mL), final concentration: 40 μM;
   f. The quantities not in current use were stored at room temperature, and were vortexed before use.

Practical Steps of the L-AD Process
1. Sample Preparation and Storage
   a. Samples thawed after freezing (−20° C.) were centrifuged (300×G/3 min)
   b. ⅔ of the supernatant was carefully pipetted into a new PCR tube, and then after homogenisation 1×2.2 μL was taken out of it, and later an aliquot of 1.1 μL was taken out.
   c. The aliquots were frozen (−75° C.), and a BioBank documentation was compiled.
2. Sample Processing:
   a. From the 2.2-μL sample (thawed after freezing), a volume of 1.4 μL was taken out;
   b. Furthermore, 0.5 μL was used for protein determination (BisANS protein assay);
   c. Based on the measured protein concentration, it was normalised to a concentration of 1.5 mg/mL using distilled water;
   d. (1) During the preliminary experiment native teardrops (2×1 μL) from the given diluted sample were applied to the hydrophobic plastic surface (Petri), and an aliquot of 1 μL of the remainder was pipetted into a new PCR tube. Next, 6.5 μL of the L-AD solution was added while stirring with a pipette. The final protein concentration of the mixture thus obtained: 0.2 mg/mL. The treated sample was also pipetted into the Petri dish (min. 3×1-μL drops);
   d. (2) During the test, 1 μL of the given diluted sample was pipetted into a new PCR tube. Next, 6.5 μL of the L-AD solution was added while stirring with a pipette. The final protein concentration of the mixture thus obtained: 0.2 mg/mL. The treated sample was pipetted to the hydrophobic plastic (Petri) surface (a drop of 1 μL);
   e. About 20 minutes of drying was required for the L-AD stagograms to develop (relative moisture content: about 50%);
   f. After taking the photographs, the Petri dishes were encoded and archived (completely wrapped with parafilm to prevent moisture from entering).

Figure 8:
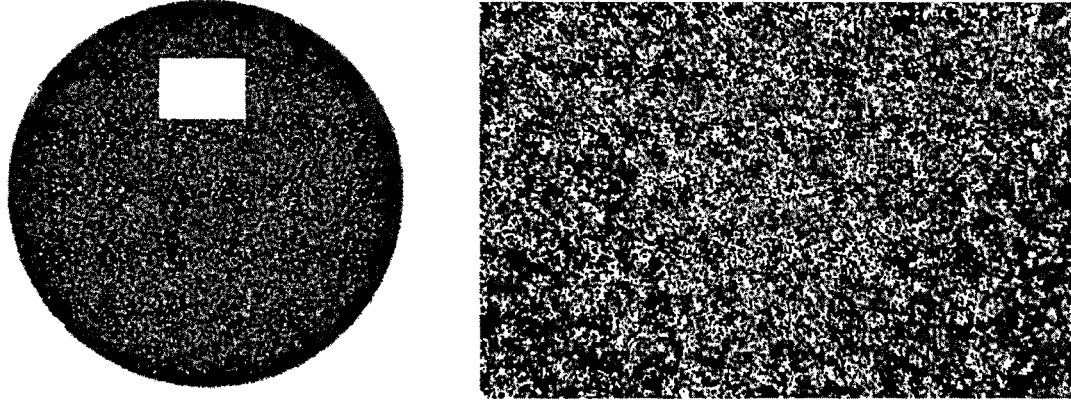
FIG. 8 shows an overview image (circular disk-shaped image) and a high-resolution image (rectangular image).

Taking Photographs of the Samples
   a. (1) During the preliminary experiment a minimum of 2 native normalised drops were photographed from one sample (depending on the available amount of sample with a protein concentration of 1.5 mg/mL), and a minimum of 3 overall photographs were taken of the normalised drops treated with the L-AD solution (circular disk-shaped) (see FIG. 2, column B) and the high-resolution photographs (rectangular shaped) (see FIG. 2, column C) were taken in the same number;
   a. (2) During the test, from the dried samples of each individual for the analysis of the area/particle ratio a minimum of 1 high-resolution photograph (rectangular shaped) (see FIG. 2, column C) was taken of the normalised (protein concentration: 1.5 mg/mL) drops treated with the L-AD solution and dried;
   b. The high-resolution photograph was taken at half of the radius of the drop (see FIG. 8).
   c. All RAW/NEF photos were archived. After the RAW-TIFF conversion, a graphical image was generated.

The invention claimed is:
1. An aqueous solution of
$AuCl_3 \times 2H_2O$ or $HAuCl_4 \times 4H_2O$,
$ZnCl_2$ or $ZnSO_4$, and
$AgNO_3$,
which comprises
$Au^{3+}$ at a concentration of 0.8 mM to 1.6 mM,
$Zn^{2+}$ at a concentration of 15 μM to 50 μM, and
$Ag^+$ at a concentration of 5 μM to 50 μM.
2. The solution according to claim 1, wherein the solution comprises the $Au^{3+}$, $Zn^{2+}$, and $Ag^+$ ions in the following molar ratio: $Au^{3+}:Zn^{2+}:Ag^+=50:1:2$.
3. The solution according to claim 1, wherein the solution is an aqueous solution of $AuCl^3 \times 2H_2O$, $ZnCl_2$ and $AgNO_3$ comprising
$Au^{3+}$ at a concentration of about 1 mM,
$Zn^{2+}$ at a concentration of about 20 μM, and
$Ag^+$ at a concentration of about 40 μM.
4. A method of preparing a solution of claim 1, the method comprising:
   (a) dissolving $AuCl_3 \times 2H_2O$ or $HAuCl_4 \times 4H_2O$ in distilled or deionised water to obtain a solution with an $Au^{3+}$ concentration of about 2 to 4 mM;
   (b) optionally freezing the solution at a temperature of −20° C. and then thawing it before step (c);
   (c) filtering the solution with an $Au^{3+}$ concentration of about 2 to 4 mM through a bacterial filter of a maximum pore size of 0.45 μm, and then mixing the filtrate with distilled or deionised water to obtain a solution with an $Au^{3+}$ concentration of about 0.8 to 1.6 mM;

(d) adding a solution with a $Zn^{2+}$ concentration of about 50 mM prepared using $ZnCl_2$ or $ZnSO_4$ and distilled or deionised water to the solution with an $Au^{3+}$ concentration of about 0.8 to 1.6 mM to obtain a solution with a $Zn^{2+}$ concentration of about 15 to 50 μM;

(e) adding a solution with an $Ag^+$ concentration of about 50 mM prepared using $AgNO_3$ and distilled or deionised water to the solution with an $Au^{3+}$ concentration of about 0.8 to 1.6 mM and $Zn^{2+}$ concentration of about 15 to 50 μM, and, optionally, stirring the solution thus obtained.

5. A method of preparing a solution of claim 3, the method comprising:

(a) dissolving $AuCl_3 \times 2H_2O$ in distilled or deionised water to obtain a solution with an $Au^{3+}$ concentration of about 2 mM;

(b) optionally freezing the solution to a temperature of −20° C., and then thawing it before step (c);

(c) filtering the solution with an $Au^{3+}$ concentration of about 2 mM through a bacterial filter with a maximum pore size of 0.45 μm, and then mixing it with distilled or deionised water to obtain a solution with an $Au^{3+}$ concentration of about 1 mM;

(d) adding a solution with a $Zn^{2+}$ concentration of about 50 mM prepared using $ZnCl_2$ and distilled or deionised water to the solution with an $Au^{3+}$ concentration of about 1 mM to obtain a solution with a $Zn^{2+}$ concentration of about 20 μM;

(e) adding a solution with an $Ag^+$ concentration of about 50 mM prepared using $AgNO_3$ and distilled or deionised water to the solution with an $Au^{3+}$ concentration of about 1 mM and $Zn^{2+}$ concentration of about 20 μM, and, optionally, stirring the solution thus obtained.

6. A solution formed by the method of claim 4, wherein the solution comprises the $Au^{3+}$, $Zn^{2+}$, and $Ag^+$ ions in the following molar ratio: $Au^{3+}:Zn^{2+}:Ag^+=50:1:2$.

7. A solution formed by the method of claim 4 wherein the solution is an aqueous solution of $AuCl_3 \times 2H_2O$, $ZnCl_2$ and $AgNO_3$ comprising $Au^{3+}$ at a concentration of about 1 mM, $Zn^{2+}$ at a concentration of about 20 μM, and $Ag^+$ at a concentration of about 40 μM.

* * * * *